US012661040B2

(12) United States Patent
Yang

(10) Patent No.: US 12,661,040 B2
(45) Date of Patent: Jun. 23, 2026

(54) BLOOD COLLECTION NEEDLE

(71) Applicant: TIANJIN RILIFINE MEDICAL DEVICE CO., LTD., Tianjin (CN)

(72) Inventor: Jiantao Yang, Tianjin (CN)

(73) Assignee: TIANJIN RILIFINE MEDICAL DEVICE CO., LTD., Tianjin (CN)

( * ) Notice: Subject to any disclaimer, the term of this patent is extended or adjusted under 35 U.S.C. 154(b) by 577 days.

(21) Appl. No.: 18/360,008

(22) Filed: Jul. 27, 2023

(65) Prior Publication Data

US 2023/0363673 A1    Nov. 16, 2023

Related U.S. Application Data

(63) Continuation of application No. PCT/CN2022/074747, filed on Jan. 28, 2022.

(30) Foreign Application Priority Data

Jul. 2, 2021    (CN) .......................... 202110750452.1
Jul. 2, 2021    (CN) .......................... 202110751401.0

(51) Int. Cl.
*A61B 5/15*        (2006.01)
*A61B 5/151*       (2006.01)

(52) U.S. Cl.
CPC .... *A61B 5/150022* (2013.01); *A61B 5/15113* (2013.01); *A61B 5/15117* (2013.01)

(58) Field of Classification Search
CPC .......... A61B 5/150022; A61B 5/15113; A61B 5/15117; A61B 5/150412;
(Continued)

(56) References Cited

U.S. PATENT DOCUMENTS

2008/0039886 A1*   2/2008   Shi ................... A61B 5/150519
606/182

FOREIGN PATENT DOCUMENTS

CN        1586396 A      3/2005
CN        1961828 A      5/2007
(Continued)

OTHER PUBLICATIONS

Office Action for CN application 2021107504521, mailed Oct. 29, 2025 (Chinese and English language translation) (15 pages).
(Continued)

*Primary Examiner* — Brooke Labranche
(74) *Attorney, Agent, or Firm* — Maginot, Moore & Beck, LLP

(57) ABSTRACT

The present disclosure provide a blood collection needle, including a cylinder body provided with a needle core and a needle body therein, in which the needle body is disposed in the needle core and a needle point of the needle body protrudes from a front end of the needle core, and a convex strip extending in a front-rear direction is disposed on an inner peripheral wall of the cylinder body; a launch spring disposed in the cylinder body, stopped against between the cylinder body and the needle core, and configured to press the needle core forward; a launch sleeve having a pushing portion, disposed in the cylinder body and movable from a first position to a second position in the front-rear direction; and a connecting ring disposed in the cylinder body and located in rear of the launch sleeve.

20 Claims, 11 Drawing Sheets

(58) Field of Classification Search
CPC ........ A61B 5/150717; A61B 5/150908; A61B
5/150503; A61B 5/150564; A61B
5/150587; A61B 5/15111
See application file for complete search history.

(56) References Cited

FOREIGN PATENT DOCUMENTS

| | | | |
|----|------------|---|--------|
| CN | 102309331  | A | 1/2012 |
| CN | 202235388  | U | 5/2012 |
| CN | 203042259  | U | 7/2013 |
| CN | 103989484  | A | 8/2014 |
| CN | 204562177  | U | 8/2015 |
| CN | 106264562  | A | 1/2017 |
| CN | 107007289  | A | 8/2017 |
| CN | 111436951  | A | 7/2020 |
| CN | 112603310  | A | 4/2021 |
| CN | 113476044  | A | 10/2021 |
| JP | 2009125312 | A | 6/2009 |
| WO | 2006029556 | A1 | 3/2006 |
| WO | 2021054684 | A1 | 3/2021 |

OTHER PUBLICATIONS

Office Action for corresponding CN application 202110750452.1, mailed May 23, 2025 (14 pages).
Office Action for corresponding CN application 202110751401.0, mailed Aug. 15, 2022 (13 pages).
Notice of Allowance for corresponding CN application 202110751401. 0, mailed Jan. 28, 2023 (9 pages).
International Search Report corresponding to PCT Application No. PCT/CN2022/074747, mailed Mar. 25, 2022 (Chinese and English language document) (6 pages).

* cited by examiner front ◄—A—► rear front — A — rear front — A — rear front — A — rear front —A— rear front ◄—A—► rear

21

22

21

22

BLOOD COLLECTION NEEDLE

CROSS-REFERENCE TO RELATED APPLICATION

The present application is a continuation application of International Application PCT/CN2022/074747, filed Jan. 28, 2022, which claims priority to Chinese Patent Application No. 202110750452.1, filed with the China National Intellectual Property Administration on Jul. 2, 2021, and Chinese Patent Application No. 202110751401.0, filed with the China National Intellectual Property Administration on Jul. 2, 2021, the contents of which are incorporated herein by reference in their entireties for all purposes.

FIELD

The present disclosure relates to a field of a medical blood collection device, and more particularly to a blood collection needle.

BACKGROUND

A blood collection needle is a kind of medical blood collection device. In related art, the blood collection needle includes a disposable blood collection needle, which can only be launched once. The development of the blood collection needle has a history of many years, and the improvement of the blood collection needle has also gone through different stages, but the blood collection needle in the related art still has the problems of convenience in operation and safety in use.

SUMMARY

The present disclosure aims to solve one of the problems existing in the related art to at least some extent.

The blood collection needle provided by the present disclosure includes: a cylinder body provided with a needle core and a needle body therein, in which the needle body is disposed in the needle core and a needle point of the needle body protrudes from a front end of the needle core, and a convex strip extending in a front-rear direction is disposed on an inner peripheral wall of the cylinder body; a launch spring disposed in the cylinder body, stopped against between the cylinder body and the needle core, and configured to press the needle core forward; a launch sleeve having a pushing portion, disposed in the cylinder body and movable from a first position to a second position in the front-rear direction; and a connecting ring disposed in the cylinder body and located in rear of the launch sleeve. A front end of the connecting ring is provided with teeth and a tooth groove between adjacent teeth, and at least one of a rear end surface of the pushing portion and a front end surface of the teeth is an inclined plane. In the first position, a front end of the launch sleeve protrudes from a front end of the cylinder body, a rear end of the convex strip engages in the tooth groove, and the connecting ring stops the needle core from moving forward. When the launch sleeve moves from the first position to the second position, the pushing portion drives the connecting ring to move backward by pushing the teeth, and the convex strip is disengaged from the tooth groove, and the teeth slide relative to the pushing portion under a pressure of the launch spring to drive the connecting ring to rotate, such that the connecting ring releases the needle core, and the needle core is launched forward under a push of the launch spring.

Alternatively, a front end surface of the convex strip has an inclined plane, and in the second position, the teeth slide gradually relative to the pushing portion to engage with the inclined plane of the convex strip, so that at least one of the convex strip and the pushing portion engages in the tooth groove to stop the connecting ring from moving forward when the needle core is launched forward.

Alternatively, the rear end surface of the pushing portion and a top surface of the teeth are inclined planes.

Alternatively, the launch sleeve includes a sleeve body, and the pushing portion is disposed on an outer peripheral wall of the sleeve body and extends backward beyond a rear end surface of the sleeve body. The pushing portion is a bar-shaped block, the pushing portions are disposed in pairs, and the paired pushing portions are disposed opposite to each other in a radial direction of the sleeve body. A plurality of convex strips are provided and distributed at intervals in a circumferential direction of the cylinder body, and the pushing portion is slidably fitted in a fitting groove between adjacent convex strips.

Alternatively, a plurality of teeth are provided and distributed at even intervals in a circumferential direction of the connecting ring.

Alternatively, the needle core is provided with a limiting portion, and a stop boss is disposed on an inner peripheral wall of the connecting ring and stops the limiting portion in the first position, and the limiting portion is disengaged from the stop boss in the second position.

Alternatively, a rear end surface of the stop boss is an inclined plane, the inner peripheral wall of the connecting ring has a sliding guide groove between the stop bosses, and the limiting portion slides forward along the sliding guide groove when the needle core is launched forward.

Alternatively, an inner peripheral wall of the launch sleeve is provided with a limiting groove for limiting an extreme position of a forward movement of the needle core, and the limiting portion enters the limiting groove and slides forward along the limiting groove to the extreme position when the needle core is launched forward.

Alternatively, the inner peripheral wall of the cylinder body is provided with a cylinder body chute extending in the front-rear direction, the needle core has a sliding wing, and the sliding wing is slidably fitted in the cylinder body chute.

Alternatively, a step portion is provided on the inner peripheral wall of the cylinder body, and the launch sleeve has an elastic locking protrusion. When the launch sleeve moves from the first position to the second position, the elastic locking protrusion is locked by the step portion to prevent the launch sleeve from moving forward during forward launching of the needle core.

Alternatively, the blood collection needle includes a needle withdrawal spring. The needle withdrawal spring is disposed in the launch sleeve, and a front end of the needle withdrawal spring stops against the launch sleeve. The needle core gradually compresses the needle withdrawal spring when the needle core is launched forward, and the needle withdrawal spring pushes the needle core to move backward after the needle core moves forward to an extreme position, so that the needle point of the needle body is retracted into the launch sleeve and/or the cylinder body.

Alternatively, the blood collection needle includes a protective cap and a needle point cap, The protective cap is detachably fitted over the front end of the cylinder body, a rear end of the needle point cap extends into the cylinder body from the front end of the cylinder body, the needle point is inserted into the rear end of the needle point cap, and the needle point cap is disposed in the protective cap and linked with the protective cap, so that the protective cap drives the needle point cap to disengage from the needle point when the protective cap is disengaged from the cylinder body.

Alternatively, at least one of the needle point cap and the needle core has a breakable portion, the front end of the needle core and the rear end of the needle point cap are integrally connected through the breakable portion, and the breakable portion is broken to allow the needle point cap to disengage from the needle point when the protective cap drives the needle point cap to move.

Alternatively, the needle point cap is disposed separately from the needle core, the rear end of the needle point cap abuts against the front end of the needle core, and the protective cap is in an interference fit with the cylinder body.

Alternatively, a front end of the needle point cap is provided with a first limiting portion, an inner peripheral wall of the protective cap is provided with a second limiting portion, and the first limiting portion is locked with the second limiting portion so that the needle point cap is linked with the protective cap.

Alternatively, the first limiting portion and the second limiting portion are locked to limit a relative translation of the needle point cap and the protective cap in the front-rear direction and a relative rotation of the needle point cap and the protective cap in a circumferential direction of the protective cap.

Alternatively, the first limiting portion is a locking groove disposed in an outer peripheral wall of the needle point cap, the second limiting portion is an elastic locking claw disposed on the inner peripheral wall of the protective cap, and a free end of the elastic locking claw is locked in the locking groove.

Alternatively, the elastic locking claw extends obliquely forward from the inner peripheral wall of the protective cap.

Alternatively, a plurality of locking grooves are provided and disposed at intervals around a circumferential direction of the needle point cap, a plurality of elastic locking claws are provided and disposed at intervals around the circumferential direction of the protective cap, and the elastic locking claws are fitted in the locking grooves in a one-to-one correspondence.

Alternatively, a step is provided on an outer peripheral wall of the front end of the needle point cap, and a locking deck for stopping the step is provided on the inner peripheral wall of the protective cap.

Alternatively, the locking deck is fan-shaped, two locking decks are provided opposite to each other and spaced apart from each other, the front end of the needle point cap is formed as a flat portion, and the flat portion is fitted between the two locking decks.

REFERENCE NUMERALS

Figure 1:
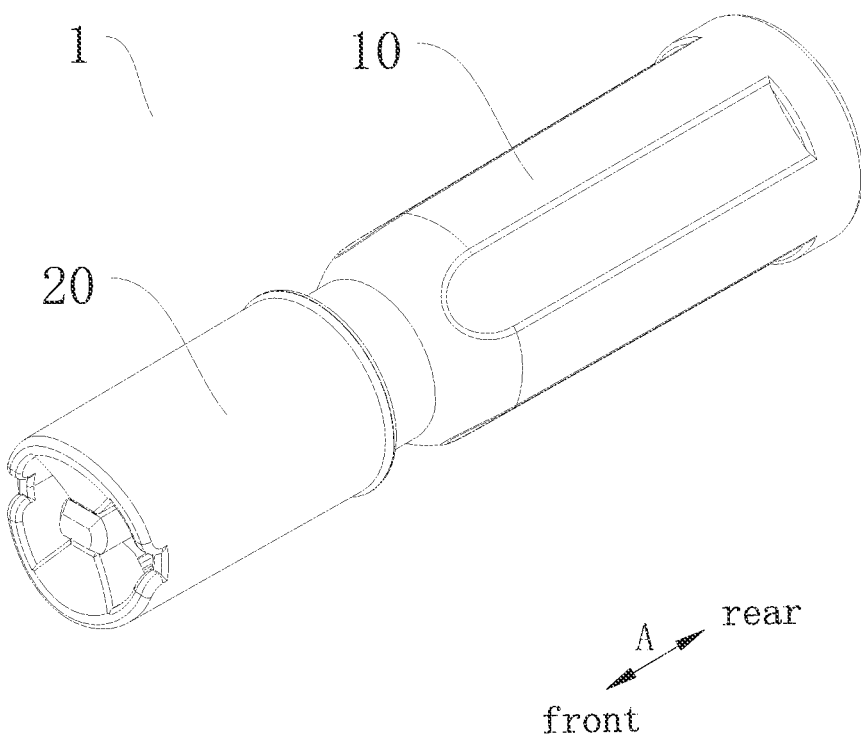
FIG. 1 is a schematic diagram of a blood collection needle according to an embodiment of the present disclosure.

1: blood collection needle; 10: cylinder body; 110: needle body; 111: needle point; 120: convex strip; 121: fitting groove; 122: first convex strip; 123: second convex strip; 130: cylinder body chute; 140: step portion; 20: protective cap; 21: elastic locking claw; 22: locking deck; 30: needle point cap; 31: breakable portion; 32: locking groove; 33: step; 34: flat portion; 40: needle core; 41: limiting portion; 42: sliding wing; 50: launch spring; 60: launch sleeve; 61: pushing portion; 62: sleeve body; 63: limiting groove; 64: elastic locking protrusion; 70: connecting ring; 71: teeth; 72: tooth groove; 73: meshing surface; 731: first meshing surface; 732: second meshing surface; 74: stop boss; 75: sliding guide groove; 80: needle withdrawal spring; 90: rear cover.

DETAILED DESCRIPTION

Embodiments of the present disclosure are described in detail below, examples of which are illustrated in the accompanying drawings. The embodiments described below with reference to drawings are explanatory, and used to explain the present disclosure. The embodiments shall not be construed to limit the present disclosure.

The following describes a blood collection needle 1 of embodiments of the present disclosure according to FIG. 1 to FIG. 17. The blood collection needle 1 of embodiments of the present disclosure includes a cylinder body 10, a launch spring 50, a launch sleeve 60 and a connecting ring 70.

The cylinder body 10 has opposite front end and rear end in its axial direction (a front-rear direction, as shown by an arrow of A in FIG. 1), and the front end of the cylinder body 10 is used as a launch end. The cylinder body 10 is provided with a needle core 40 and a needle body 110, an axial direction of the needle core 40 and the needle body 110 extends in the front-rear direction. A needle point 111 of the needle body 110 is its front end, and the needle body 110 is disposed in the needle core 40 and the needle point 111 of the needle body 110 protrudes from a front end of the needle core 40. A convex strip 120 extending in the front-rear direction is disposed on an inner peripheral wall of the cylinder body 10. A launch spring 50 is disposed in the cylinder body 10, stops against between the cylinder body 10 and the needle core 40, and is configured to press the needle core 40 forward. The needle core 40 may be launched forward under a role of the launch spring 50, the needle core 40 is launched forward to drive the needle body 110 forward, and the needle point 111 of the needle body 110 is pushed out from the front end of the cylinder body 10 to implement the blood collection function.

The launch sleeve 60 has a pushing portion 61, and the launch sleeve 60 is disposed in the cylinder body 10 and movable from a first position to a second position in the front-rear direction, that is, the launch sleeve 60 moves backward so that the launch sleeve 60 moves from the first position to the second position. A connecting ring 70 is disposed in the cylinder body 10 and is located behind the launch sleeve 60, and a front end of the connecting ring 70 is provided with teeth 71 and a tooth groove 72 between adjacent teeth 71. At least one of a rear end surface of the pushing portion 61 and a front end surface of the teeth 71 has an inclined plane.

In the first position, a front end of the launch sleeve 60 protrudes from the front end of the cylinder body 10, a rear end of the convex strip 120 engages in the tooth groove 72, and the connecting ring 70 stops the needle core 40 from moving forward. That is to say, the front end of the launch sleeve 60 in the first position is located outside the cylinder body 10, and the rear end of the convex strip 120 extends backward into the tooth groove 72 of the connecting ring 70 and abuts against a groove bottom of the tooth groove 72 to stop the connection ring 70 from moving forward, and the connection ring 70 prevents the needle core 40 from moving forward.

When the launch sleeve 60 moves backward from the first position to the second position, the pushing portion 61 of the launch sleeve 60 drives the connecting ring 70 to move backward by pushing the teeth 71 of the connecting ring 70, the convex strip 120 is disengaged from the tooth groove 72, and the teeth 71 slide relative to the pushing portion 61 under a pressure of the launch spring 50 to rotate the connecting ring 70, such that the connecting ring 70 releases the needle core 40 and the needle core 40 is launched forward under a push of the launch spring 50.

That is to say, in a process of moving backward of the launch sleeve 60, the rear end surface of the pushing portion 61 of the launch sleeve 60 abuts against the front end surface of the teeth 71 of the connecting ring 70, so that the launch sleeve 60 pushes the connecting ring 70 to move backward. The connecting ring 70 moves backward, so that the convex strip 120 is disengaged gradually from the tooth groove 72. After the convex strip 120 is disengaged completely from the tooth groove 72, the convex strip 120 loses its stop on the connecting ring 70. Since the launch spring 50 presses the needle core 40 forward, and the connecting ring 70 stops against the needle core 40, and since at least one of the rear end surface of the pushing portion 61 and the front end surface of the teeth 71 is the inclined plane, the teeth 71 and the pushing portion 61 slide relative to each other after the convex strip 120 is disengaged completely from the tooth groove 72. In an embodiment, a relative position between the cylinder body 10 and the launch sleeve 60 and its pushing portion 61 remains unchanged, and the connecting ring 70 and its teeth 71 rotate relative to the cylinder body 10. Since a rotation of the connecting ring 70 makes the connecting ring 70 no longer stop against the needle core 40, the needle core 40 loses a limitation of the connecting ring 70 and is launched forward under the push of the launch spring 50, and finally the needle head of the needle body 110 in the needle core 40 is exposed forwardly from the front end of each of the launch sleeve 60 and the cylinder body 10 to implement the blood collection function.

When the launch sleeve 60 is located in the first position, the front end of the launch sleeve 60 protrudes from a front end of a sleeve, the rear end of the convex strip 120 of the cylinder body 10 engages in the tooth groove 72 of the connecting ring 70 to stop the connecting ring 70, and the connecting ring 70 stops against the needle core 40 from moving forward. At this moment, the needle head of the needle body 110 is located inside the blood collection needle 1, that is, the needle body 110 is in a non-launched state. The front end of the launch sleeve 60 may press the skin, the cylinder body 10 is held to push the cylinder body 10 forward (close to the skin), and the launch sleeve 60 moves backward relative to the cylinder body 10 and moves from the first position to the second position. In this process, the rear end surface of the pushing portion 61 of the launch sleeve 60 abuts against the front end surface of the teeth 71 of the connecting ring 70, so that the launch sleeve 60 pushes the connecting ring 70 backward, and finally the convex strip 120 is disengaged from the tooth groove 72 completely. Under the pressure of the launch spring 50, the teeth 71 slides relative to the pushing portion 61. Since at least one of the rear end surface of the pushing portion 61 and the front end surface of the teeth 71 is the inclined plane, the sliding of the teeth 71 of the connecting ring 70 relative to the pushing portion 61 is expressed as a rotation of the connecting ring 70. The connecting ring 70 rotates to allow the needle core 40 to be released. The needle core 40 is launched forward under the push of the launch spring 50, and the needle head is launched from forward and exposed from the front end of each of the launch sleeve 60 and the cylinder body 10, so as to insert into the skin located in front of the launch sleeve 60 to implement the blood collection.

According to the blood collection needle 1 of an embodiment of the present disclosure, a launch of the needle core 40 in the cylinder body 10 is implemented through the cylinder body 10, the launch spring 50, the launch sleeve 60 and the connecting ring 70 that interact with each other. When the blood collection needle 1 is not in use, the teeth 71 on the cylinder body 10, the connecting ring 70 and the needle core 40 stop against each other, so that the needle body 110 and its needle point 111 are hidden safely inside the cylinder body 10, which has a high safety. When the blood collection needle 1 is in use, the cylinder body 10 is only needed to hold, making the front end of the launch sleeve 60 touch the skin. The cylinder body 10 is moved forward to make the launch sleeve 60 and the cylinder body 10 slide relative to each other, so that the needle core 40 and the needle body 110 are launched together, which has the simple operation, the reasonable structure and the reliable performance.

The structure, the assembly process and the operation process of the blood collection needle 1 of embodiments of the present disclosure will be further described below in conjunction with FIG. 1 to FIG. 17.

Figure 9:
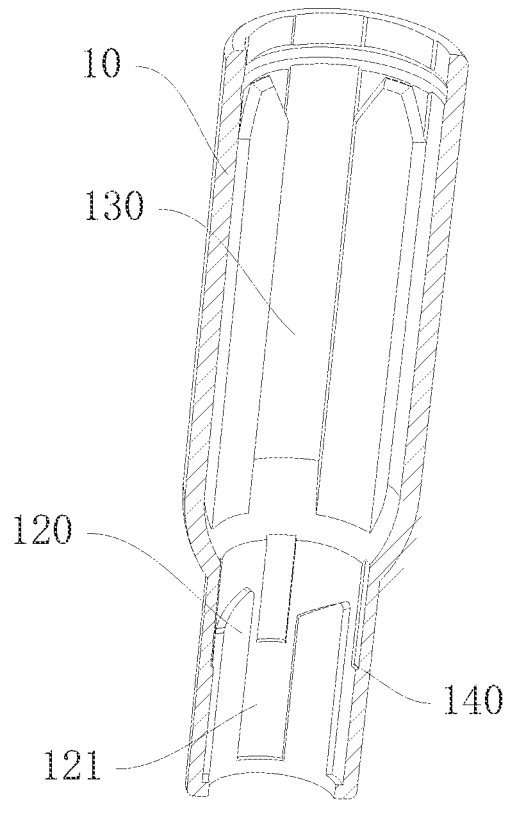
FIG. 9 is a cross-sectional view of a cylinder body according to an embodiment of the present disclosure.
Figure 10:
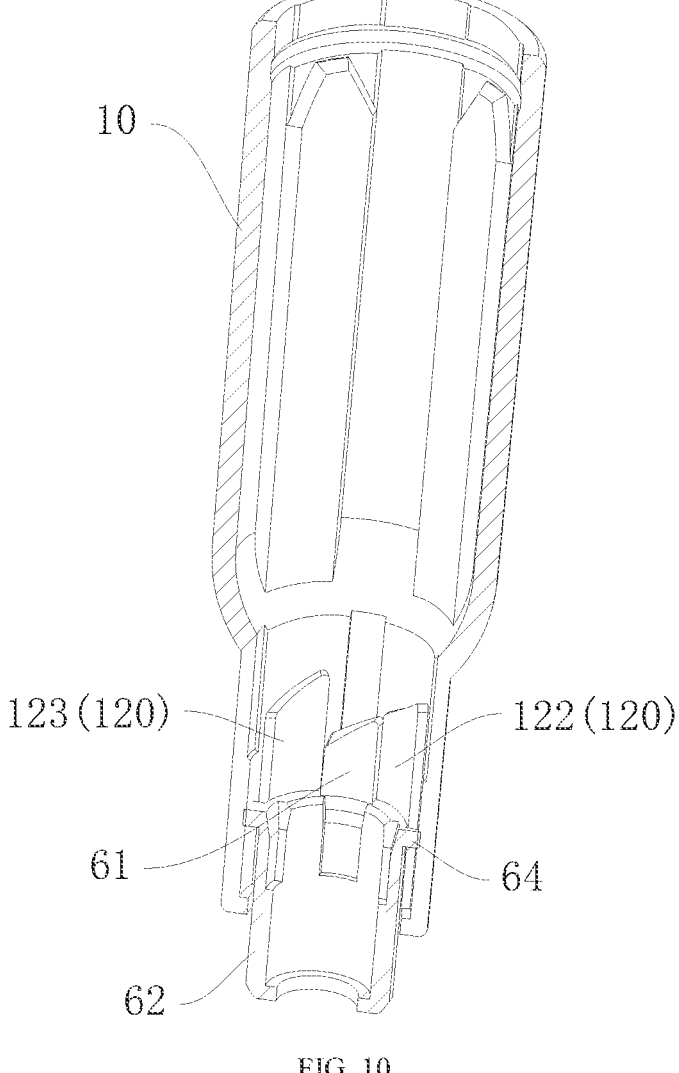
FIG. 10 is a partial sectional view of a blood collection needle according to an embodiment of the present disclosure.

As shown in FIG. 9, an inner peripheral wall of the cylinder body 10 is provided with four convex strips 120 extending in the front-rear direction. The four convex strips 120 are distributed at equal intervals in a circumferential direction of the cylinder body 10, and a fitting groove 121 extending in the front-rear direction is formed between adjacent convex strips 120.

Further, in order to better guide the rotation of the connecting ring 70, a front end surface of the convex strip 120 is an inclined plane. In the second position, the teeth 71 of the connecting ring 70 slid gradually relative to the pushing portion 61 of the launch sleeve 60 to a position where the inclined plane of the convex strip 120 engages, so that at least one of the convex strip 120 and the pushing portion 61 engages in the tooth groove 72 to stop the connecting ring 70 from moving forward when the needle core 40 is launched forward.

It is understood that, in other embodiments, a number of the convex strips 120 may be more than one, and may not be four, which is not limited here. The plurality of convex strips 120 are distributed at intervals in the circumferential direction of the cylinder body 10 and which is not limited to be equally spaced. In an embodiment, the convex strips 120 are disposed in pairs, and the paired convex strips 120 are disposed opposite to each other in a radial direction of the cylinder body 10.

That is to say, when the launch sleeve 60 moves backward to the second position, and the teeth 71 of the connecting ring 70 slides relative to the pushing portion 61 of the launch sleeve 60, the teeth 71 slides gradually along the inclined plane of the convex strip 120 until the teeth 71 is engaged with the inclined plane of the convex strip 120, so that when the needle core 40 is launched forward, the convex strip 120 and/or the pushing portion 61 stops against a bottom of the tooth groove 72 to stop the connecting ring 70 from moving further.

Furthermore, in order to further improve the structural reliability of the connecting ring 70 when the connecting ring 70 rotates relative to the launch sleeve 60, a rear end surface of the pushing portion 61 and a top surface of the teeth 71 are both the inclined planes, and the rear end surface of the pushing portion 61 cooperates with the top surface of the teeth 71. Furthermore, an inclination angle between the rear end surface of the pushing portion 61 and the top surface of the teeth 71 is same as an inclination angle of the front end surface of the convex strip 120.

Figure 11:
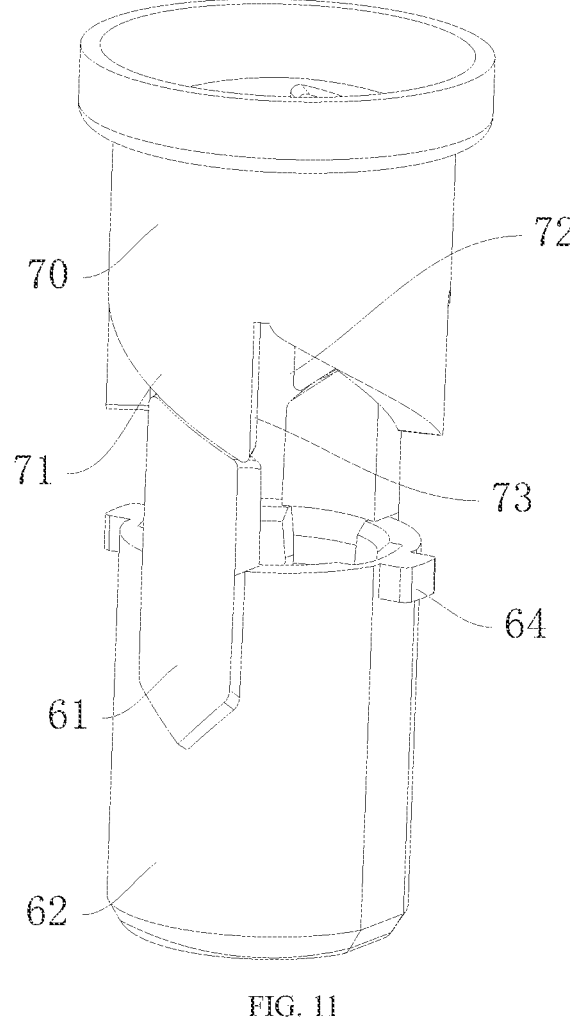
FIG. 11 is a structural diagram of a part of a blood collection needle according to an embodiment of the present disclosure.
Figure 12:
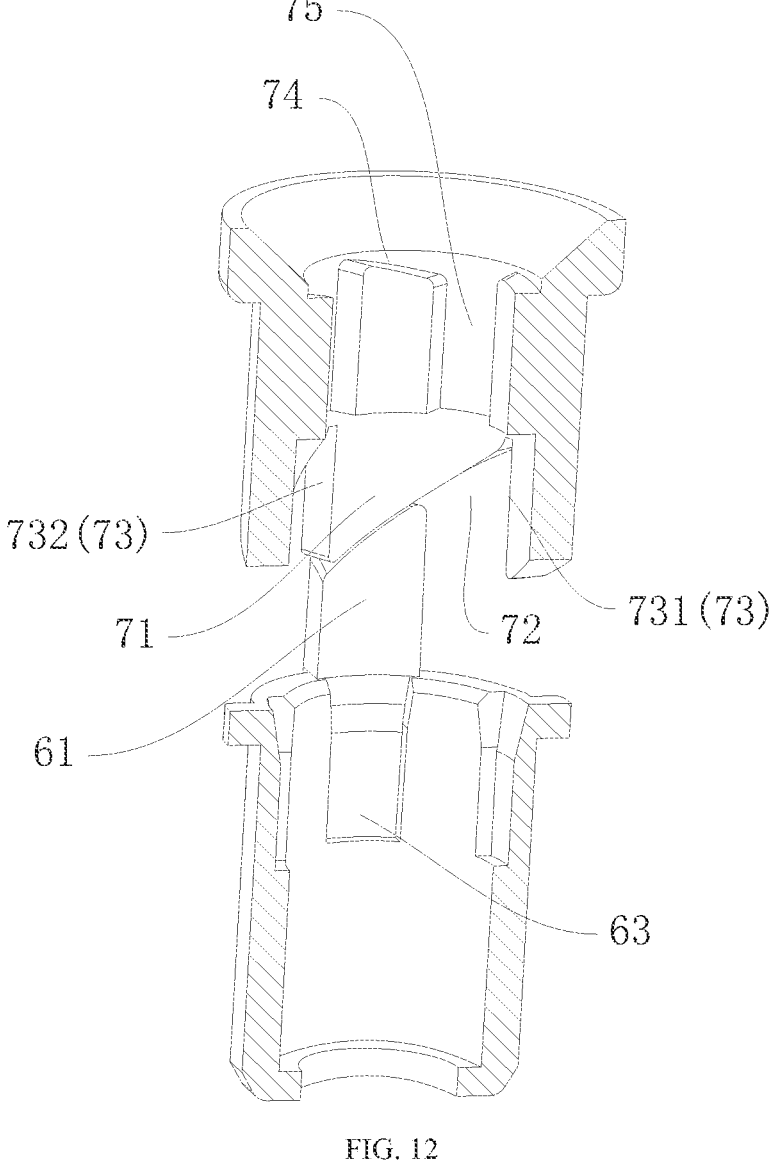
FIG. 12 is a cross-sectional view of FIG. 11.

As shown in FIGS. 11 and 12, the launch sleeve 60 includes a sleeve body 62. The pushing portion 61 is a bar-shaped block, and the pushing portion 61 is disposed on an outer peripheral wall of the sleeve body 62 and extends backward beyond a rear end surface of the sleeve body 62. As an example, a front end of the bar-block-shaped pushing portion 61 is connected to the outer peripheral wall of the sleeve body 62 and protrudes outward relative to the outer peripheral wall of the sleeve body 62, and the rear end of the pushing portion 61 is located behind the rear end surface of the sleeve body 62, that is, a part of the pushing portion 61 protrudes backward relative to the rear end surface of the sleeve body 62.

The pushing portion 61 is slidably fitted in a fitting groove 121 formed by the convex strips 120 on an inner peripheral wall of the cylinder body 10. When the launch sleeve 60 moves backward to move from the first position to the second position, the pushing portion 61 slides backward along the fitting groove 121. The fitting groove 121 plays a guiding role, and is configured to limit a rotation of the launch sleeve 60. Moreover, a cooperation of the pushing portion 61 and the fitting groove 121 facilitates an assembly of the launch sleeve 60. When the launch sleeve 60 is assembled, the launch sleeve 60 is loaded into the cylindrical body 10 from the rear end of the cylinder body 10 until the front end of the launch sleeve 60 protrudes from the front end of the cylinder body 10. In a process of the launch sleeve 60 moving from back to front, the pushing portion 61 is automatically introduced into any one of the fitting grooves 121 and slides forward along the fitting groove 121.

In some embodiments, the pushing portions 61 are disposed in pairs, and the paired pushing portions 61 are disposed opposite to each other in a radial direction of the sleeve body 62. As shown in FIG. 11 and FIG. 12, the launch sleeve 60 has two pushing portions 61 disposed opposite to each other in the radial direction of the sleeve body 62.

Furthermore, as shown in FIG. 11, the front end of the pushing portion 61 is tapered, so as to be better introduced into the fitting groove 121 during an assembly process of the launch sleeve 60.

The connecting ring 70 has a plurality of teeth 71 and is distributed at even intervals in a circumferential direction of the connecting ring 70. As shown in FIG. 11 and FIG. 12, the connecting ring 70 in embodiments of the present disclosure has four teeth 71 distributed at even intervals in the circumferential direction of the connecting ring 70. A front end surface of the teeth 71 is an inclined plane. It is understood that, in an embodiment, the front end surface of the teeth 71 shares a surface with a groove bottom surface of the tooth groove 72. There is a meshing surface 73 extending in the front-rear direction between the teeth 71 and an adjacent tooth groove 72. A front end of the meshing surface 73 and a front end of the front end surface of the teeth 71 are connected, and a rear end of the meshing surface 73 and a rear end of the front end surface of the adjacent teeth 71 are connected.

In an embodiment, a length of the front end surface (inclined plane) of the teeth 71 is equal to a sum of lengths of the rear end surface (inclined plane) of the convex strip 120 and a rear section surface of the pushing portion 61 (inclined plane). It is understood that the "length" here refers to the length of the inclined plane in its extending direction.

It is noted that, the structures of the teeth 71 and the tooth groove 72 of the connecting ring 70 in an embodiment of the present disclosure may realize 360° automatic guidance when the cylinder body 10 is assembled. When the connecting ring 70 is assembled, it is loaded from the rear end of the cylinder body 10 from back to front. Since the front end surface of the teeth 71 of the connecting ring 70 is the inclined plane, the connecting ring 70 may be automatically engaged with any one of the convex strips 120 on the cylinder body 10 without prior alignment and additional guiding measures, so that the blood collection needle 1 may be assembled conveniently and quickly.

For example, the convex strips 120 include a first convex strip 122 and a second convex strip 123, and a launch process of the blood collection needle 1 in embodiments will be described in detail below.

One pushing portion 61 on the launch sleeve 60 is fitted into the fitting groove 121 formed between the first convex strip 122 and the second convex strip 123. In the first position, the rear end surface of the pushing portion 61 is located in front of the rear end surface of the first convex strip 122, and forms a plane with the rear end surface of the first convex strip 122 in the extending direction. Each of the rear end surface of the first convex strip 122 and the rear end surface of the pushing portion 61 abuts against the front end surface of the teeth 71. A meshing surface 73 that links to the rear end of the front end surface of the teeth 71 is a first meshing surface 731, and a meshing surface 73 that links to the front end of the front end surface of the teeth 71 is a second meshing surface 732. A side surface of the first convex strip 122 abuts against the first meshing surface 731, and a side surface of the second convex strip 123 abuts against the second meshing surface 732. At this time, the blood collection needle 1 is in a to-be-launched state. The connecting ring 70 is limited in a forward direction under a common stopping against role of the first convex strip 122 and the second convex strip 123.

When the launch sleeve 60 moves from the first position to the second position, the pushing portion 61 moves backward along the fitting groove 121, and the rear end surface of the pushing portion 61 abuts against the front end surface of the teeth 71, so that under a driving of the pushing portion 61, the connecting ring 70 moves backward, and the rear end surface of the first convex strip 122 is disengaged from the front end surface of the teeth 71. The first meshing surface 731 slides backward along the side surface of the first convex strip 122, and the second meshing surface 732 slides backward along the side surface of the second convex strip 123. Under a guidance of the first convex strip 122 and the second convex strip 123, both the launch sleeve 60 and the connecting ring 70 are limited in the circumferential direction, that is, which cannot rotate.

When the launch sleeve 60 reaches the second position, the first meshing surface 731 is disengaged completely from the first convex strip 122, the second meshing surface 732 is disengaged completely from the second convex strip 123, and the first convex strip 122 and the second convex strip 123 are disengaged completely from the tooth groove 72. At this time, the rear end surface of the pushing portion 61 is located behind the rear end surface of the second convex strip 123, and forms a plane with the rear end surface of the second convex strip 123 in the extending direction. Under the pressure of the launch spring 50, the front end surface of the teeth 71 slides relative to the rear end surface of the pushing portion 61, and the front end surface of the teeth 71 gradually slides to the rear end surface of the second convex strip 123 until the front end surface of the teeth 71 and the rear end surface of the second convex strip 123 are opposite to the rear end surface of the pushing portion 61, the first meshing surface 731 abuts against the side surface of the pushing portion 61, and the second convex strip 123 and the pushing portion 61 commonly stop against the teeth 71 to prevent it from continuing to slide. In a process of relative sliding between the front end surface of the teeth 71 and the rear end surface of the pushing portion 61, the connecting ring 70 rotates forward. The rotation of the connecting ring 70 releases the needle core 40 and the needle core 40 is launched forward under a push of the launch spring 50.

Figure 13:
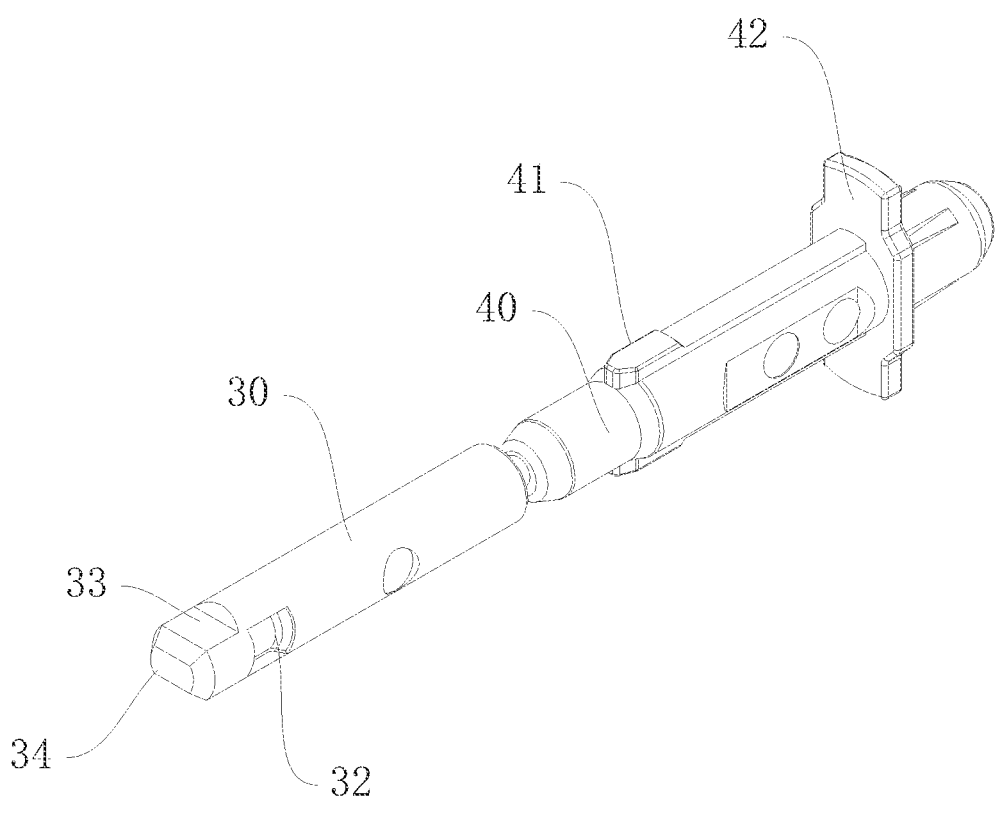
FIG. 13 is a structural diagram of a part of a blood collection needle according to an embodiment of the present disclosure.
Figure 14:
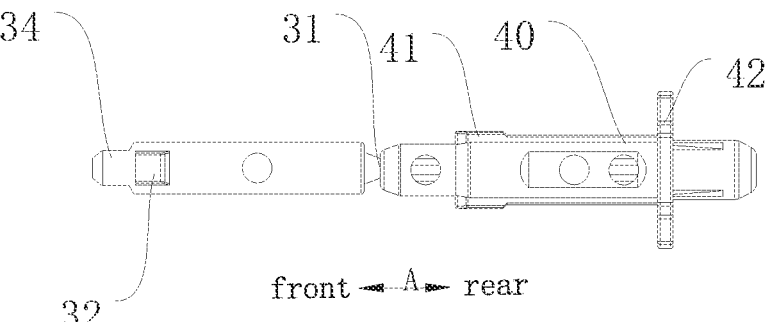
FIG. 14 is a front view of FIG. 13.
Figure 15:
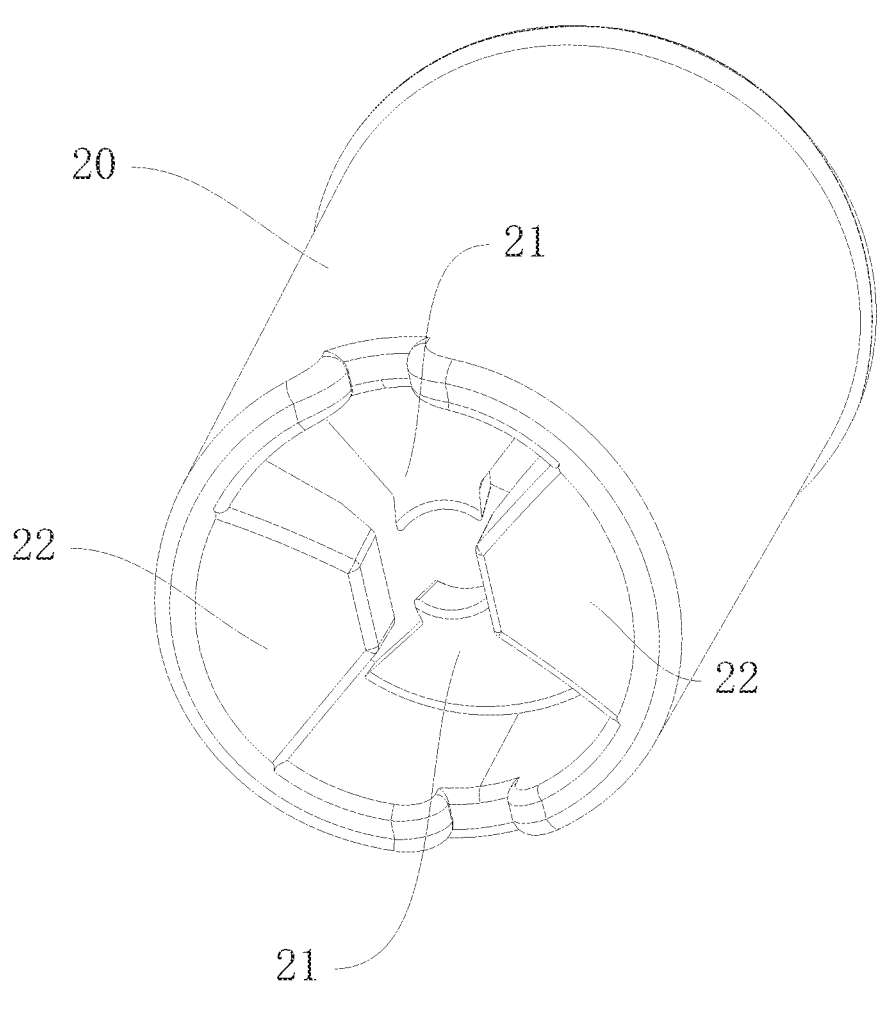
FIG. 15 is a structural diagram of a protective cap according to an embodiment of the present disclosure.
Figure 16:
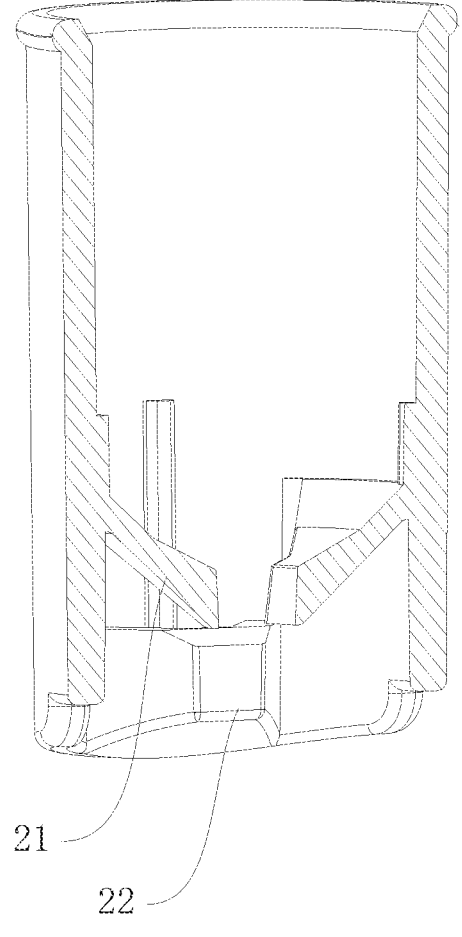
FIG. 16 is a cross-sectional view of a protective cap according to an embodiment of the present disclosure.
Figure 17:
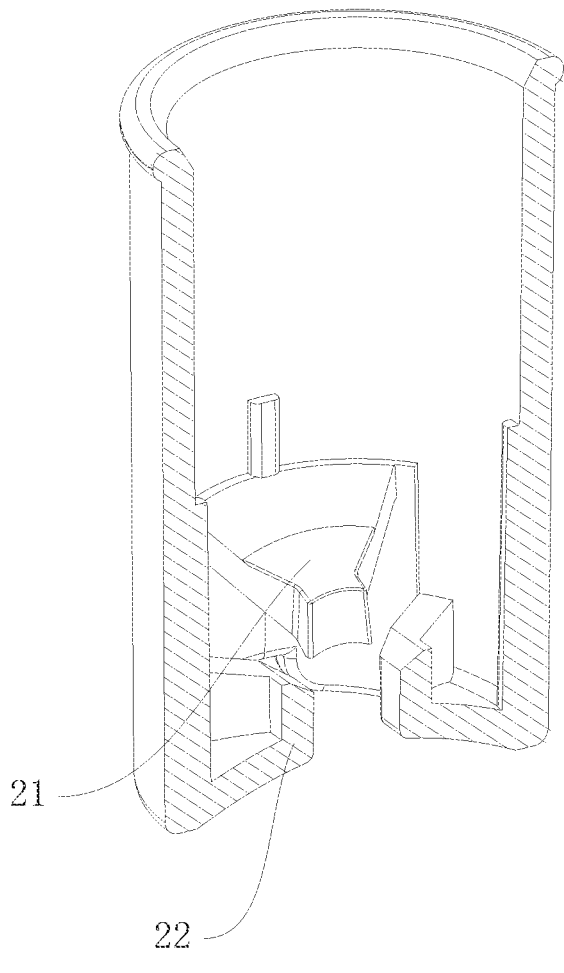
FIG. 17 is a cross-sectional view of a protective cap according to an embodiment of the present disclosure.

As shown in FIGS. 12 to 14, the needle core 40 is provided with a limiting portion 41, and the inner peripheral wall of the connecting ring 70 is provided with stop bosses 74. The stop boss 74 stops the limiting portion 41 in the first position, and the limiting portion 41 is disengaged from the stop boss 74 in the second position. In an embodiment, the front end of the launch spring 50 abuts against the rear end of the limiting portion 41, such that the launch spring 50 presses the needle core 40 forward. In the first position and during a process of moving from the first position to the second position, the front end of the limiting portion 41 abuts against the rear end of the stop boss 74, so that the connecting ring 70 drives the needle core 40 to move backward, and the needle core 40 moves backward to compress the launch spring 50. In the second position, the connecting ring 70 rotates to allow the limiting portion 41 to disengage from the stop boss 74, and the needle core 40 is no longer limited by the connecting ring 70 and is launched forward under the push of the launch spring 50. In an embodiment of the present disclosure, four stop bosses 74 are disposed on the connecting ring 70 and are distributed at equal intervals in the circumferential direction, and the needle core 40 is provided with two limiting portion 41 that are opposite to each other in the radial direction.

Furthermore, in an embodiment of the present disclosure, the rear end surface of the stop boss 74 is an inclined plane, so that when the connecting ring 70 rotates, the limiting portion 41 may be more smoothly disengaged from the stop boss 74.

As shown in FIG. 12, the stop boss 74 on the inner peripheral wall of the connecting ring 70 has a strip shape and extends in the front-rear direction, and a sliding guide groove 75 is formed between adjacent stop bosses 74. It is understood that the sliding guide groove 75 extends in the front-rear direction. When the needle core 40 is launched forward, the limiting portion 41 slides forward along the sliding guide groove 75, that is, the sliding guide groove 75 is configured to guide the needle core 40 when the needle core 40 is launched forward, so as to prevent the needle core 40 from rotating.

The inner peripheral wall of the launch sleeve 60 is provided with a limiting groove 63 extending in the front-rear direction. When the connecting ring 70 is rotated to an extreme position, the limiting groove 63 is opposite to the sliding guide groove 75 in the front-rear direction. In an embodiment of the present disclosure, two limiting grooves 63 are included and opposite to each other in the radial direction of the sleeve body 62, and the two limiting grooves 63 correspond to two pushing portions 61 of the launch sleeve 60 one-to-one. In other embodiments, four limiting grooves 63 may be provided and corresponds to four sliding guide grooves 75 one-to-one.

The limiting groove 63 is configured to limit an extreme position of a forward movement of the needle core 40. When the needle core 40 is launched forward, the limiting portion 41 enters the limiting groove 63 and slides forward along the limiting groove 63 to the extreme position. The extreme position of the needle core 40 refers to a most forward position when launching forward. Alternatively, when the needle core 40 reaches the extreme position, the front end of the needle core 40 is flush with the front end of the launch sleeve 60, and the needle point 111 is completely exposed from the front end of the launch sleeve 60. At this time, the front end of the limiting portion 41 on the needle core 40 abuts against a groove bottom of the limiting groove 63.

It is understood that, when the connecting ring 70 is rotating, in order to implement that the limiting portion 41 of the needle core 40 is disengaged from the stop boss 74, the needle core 40 should not rotate with the connecting ring 70. In order to achieve this purpose, in an embodiment, the needle core 40 and the cylinder body 10 are limited in the circumferential direction of the cylinder body 10. As shown in FIG. 9, the inner peripheral wall of the cylinder body 10 is provided with a cylinder body chute 130 extending in the front-rear direction, the needle core 40 has a sliding wing 42, and the sliding wing 42 is slidably fitted in the cylinder body chute 130. During moving from the first position to the second position, the needle core 40 moves backward, and the sliding wing 42 slides backward along the cylinder body chute 130. In the second position, since the sliding wing 42 is fitted in the cylinder body chute 130, the rotation of the needle core 40 is limited, such that the limiting portion 41 on the needle core 40 may be disengaged from the stop boss 74 smoothly.

Furthermore, a step portion 140 is provided on the inner peripheral wall of the cylinder body 10, and the launch sleeve 60 has an elastic locking protrusion 64. When the launch sleeve 60 moves from the first position to the second position, the elastic locking protrusion 64 is locked by the step portion 140 so as to prevent the launch sleeve 60 from moving forward during forward launching of the needle core 40. As an example, as shown in FIG. 9, four step portions 140 are provided on the inner peripheral wall of the cylinder body 10, and the four step portions 140 are distributed at intervals in the circumferential direction. The launch sleeve 60 has two elastic locking protrusions 64, and the two elastic locking protrusions 64 are opposite in the radial direction. The elastic locking protrusions 64 are connected to the outer peripheral wall of the sleeve body 62, and extend outward from the outer peripheral wall of the sleeve body 62. The elastic locking protrusions 64 can produce an elastic deformation. When the launch sleeve 60 moves to the second position, the elastic locking protrusion 64 is located behind the step portion 140 and abuts against a step surface of the step portion 140 forward, so as to prevent the launch sleeve 60 from moving forward when the needle core 40 is launched. After the needle core 40 is launched, the elastic locking protrusion 64 is still locked on the step portion 140, so that the launch sleeve 60 will not slide forward relative to the cylinder body 10.

Figure 2:
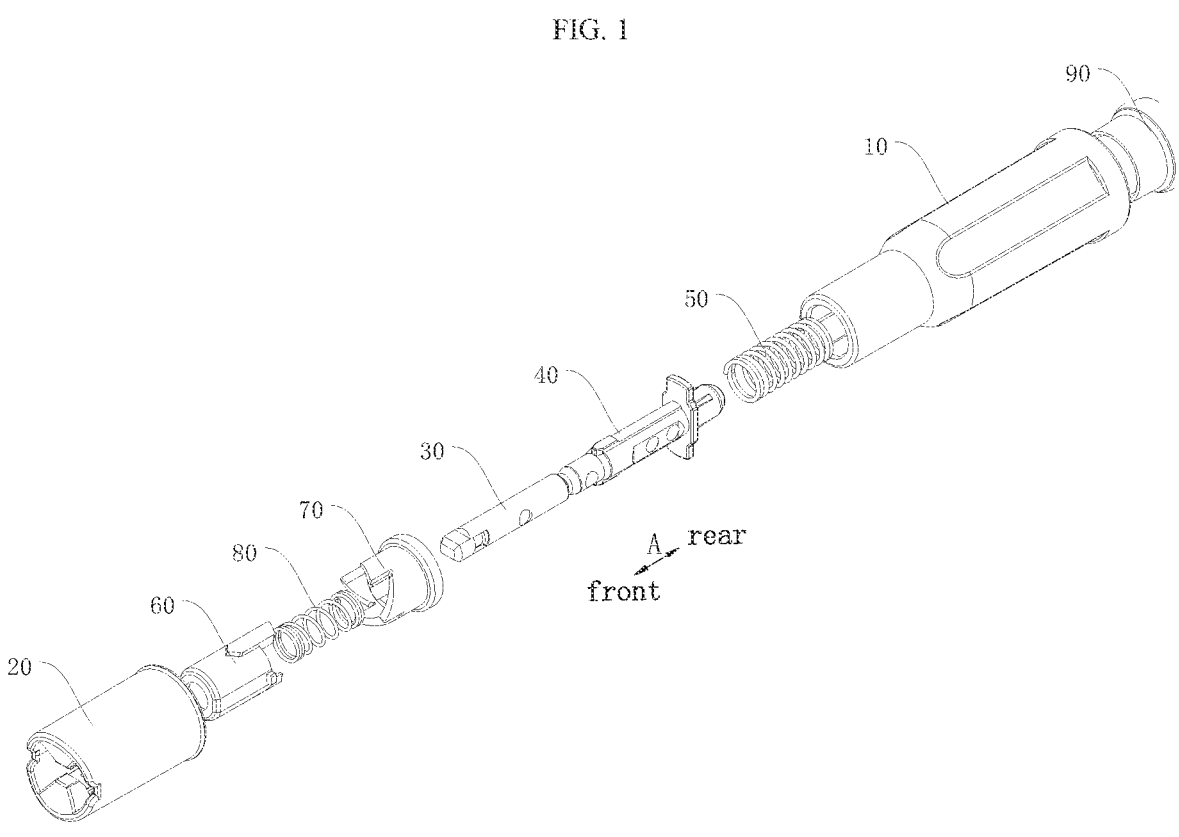
FIG. 2 is an explosion diagram of a blood collection needle according to an embodiment of the present disclosure.
Figure 3:
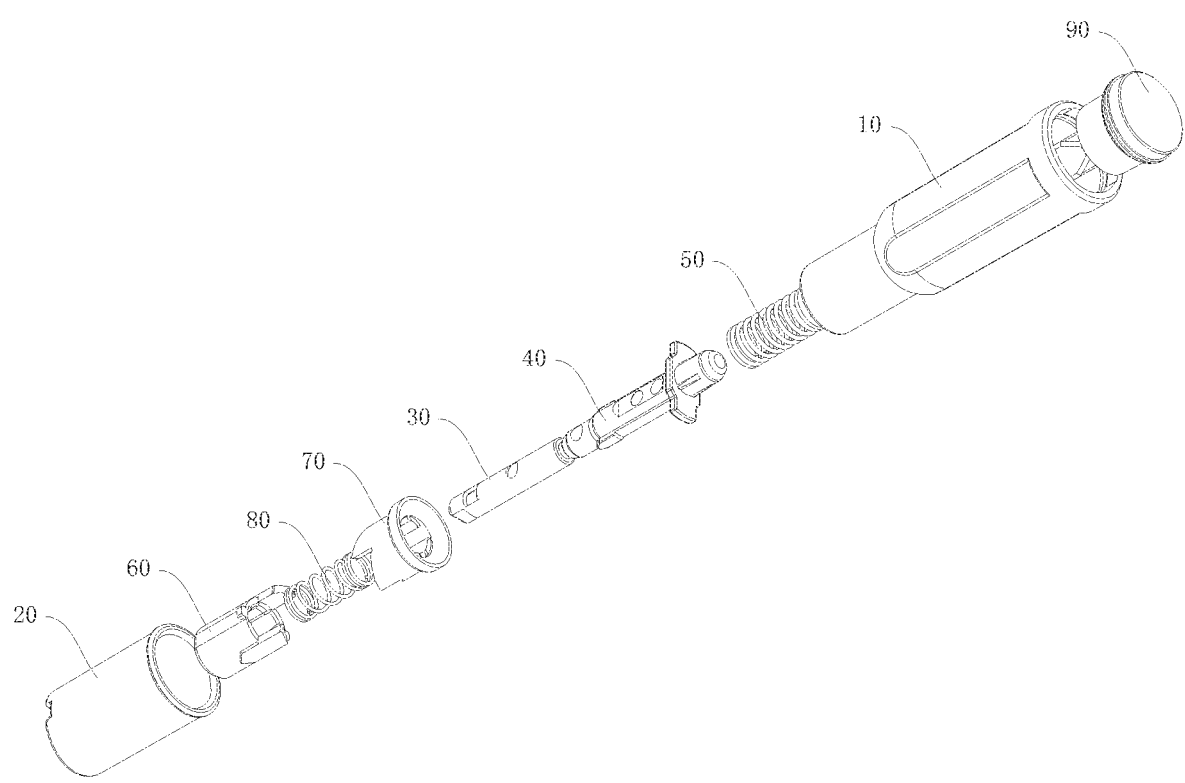
FIG. 3 is an explosion diagram of a blood collection needle according to an embodiment of the present disclosure.
Figure 6:
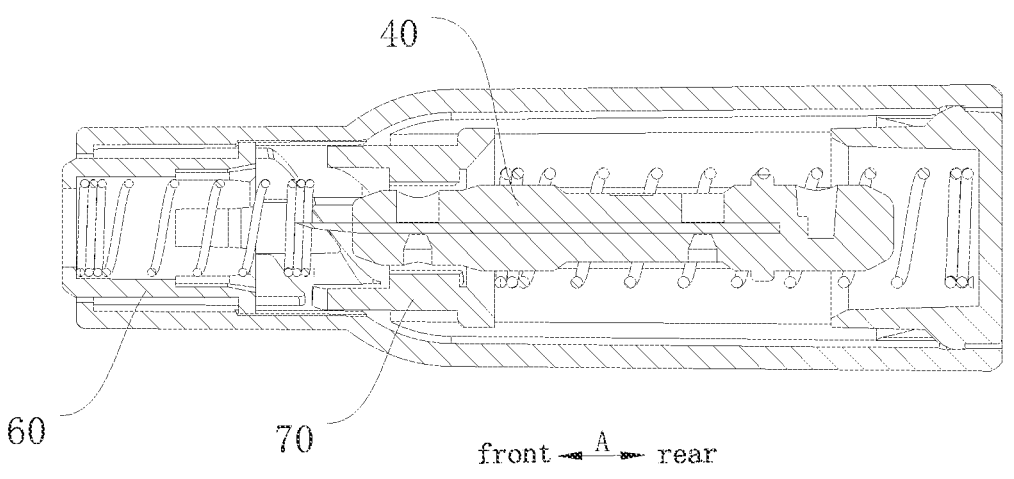
FIG. 6 is a cross-sectional view of a blood collection needle according to an embodiment of the present disclosure.

As shown in FIG. 2, the blood collection needle 1 further includes a needle withdrawal spring 80. The needle withdrawal spring 80 is disposed in the launch sleeve 60, and a front end of the needle withdrawal spring 80 abuts against the launch sleeve 60. When the needle core 40 is not launched forward, the needle withdrawal spring 80 is in a freely stretched state. As shown in FIG. 6, when the needle core 40 is launched forward, the needle core 40 gradually compresses the needle withdrawal spring 80. After the needle core 40 moves forward to an extreme position, the needle withdrawal spring 80 pushes the needle core 40 to move backward, so that the needle point 111 of the needle body 110 is retracted into the launch sleeve 60 and/or the cylinder body 10.

In an embodiment, as shown in FIG. 6, when the needle core 40 is launched forward, the front end of the limiting portion 41 abuts against a rear end of the needle withdrawal spring 80, so as to gradually compress the needle withdrawal spring 80, and the needle withdrawal spring 80 is compressed to apply a backward force on the needle core 40. When the needle core 40 moved forward to the extreme position, the backward force applied by the needle withdrawal spring 80 to the needle core 40 is greater than a forward force applied by a launch spring 50 to the needle core 40. Under the force of the needle withdrawal spring 80, the needle core 40 starts to move backward until the needle point 111 is retracted into the launch sleeve 60, such that after the blood collection needle 1 is used, the needle point 111 will not be exposed, which avoids unnecessary harm to personnel, avoids the cross-infection, and improves the safety performance of the blood collection needle 1.

Figure 4:
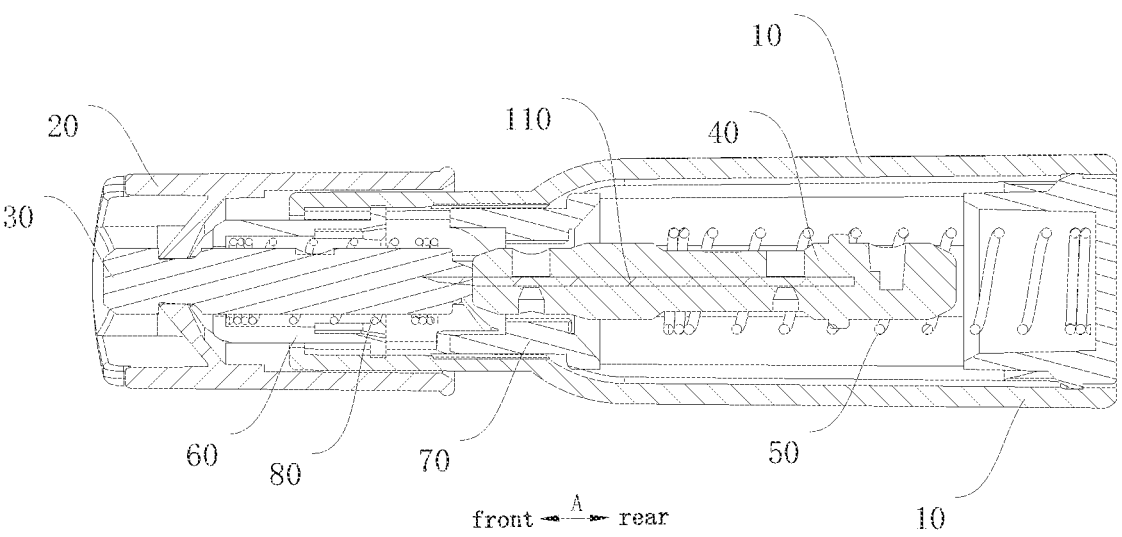
FIG. 4 is a cross-sectional view of a blood collection needle according to an embodiment of the present disclosure.

Furthermore, as shown in FIG. 4, the blood collection needle 1 includes a protective cap 20 and a needle point cap 30. The protective cap 20 is detachably fitted over a front end of the cylinder body 10. That is to say, the protective cap 20 has two states of being fitted over the front end of the cylinder body 10, and being disengaged from the front end of the cylinder body 10. It is understood that if the protective cap 20 is disengaged from the front end of the cylinder body 10, the protective cap 20 needs to be moved forward.

A rear end of the needle point cap 30 extends into the cylinder body 10 from the front end of the cylinder body 10. The needle point 111 protruding from the needle core 40 is inserted into the rear end of the needle point cap 30, and the needle point cap 30 is configured to protect the needle point 111. The needle point cap 30 is disposed in the protective cap 20, and the needle point cap 30 is linked with the protective cap 20, so that the protective cap 20 drives the needle point cap 30 to disengage from the needle point 111 when the protective cap 20 is disengaged from the cylinder body 10. That is to say, the protective cap 20 is disengaged from the front end of the cylinder body 10 to drive the needle point cap 30 to disengage from the needle point 111, so that the needle point 111 is exposed. For example, when the blood collection needle 1 is to-be-used, the protective cap 20 is fitted over the front end of the cylinder body 10 and the needle point 111 is located in the needle point cap 30 to play a protective role. When the blood collection needle 1 is required to be used, the protective cap 20 is disengaged from the front end of the cylinder body 10 (the protective cap 20 is pulled out forward) to drive the needle point cap 30 to disengage from the needle point 111 forward, so that the needle point 111 is exposed.

The blood collection needle 1 according to embodiments of the present disclosure utilizes the linkage between the protective cap 20 and the needle point cap 30 to protect and expose the needle point 111 of the needle body 110. By disengaging the protective cap 20, which is fitted over the front end of the cylinder body 10, from the cylinder body 10, the needle point cap 30 is driven to disengage from the needle point 111, so as to enable the needle point 111 to be exposed, which is simple, fast and reliable. Moreover, when the blood collection needle 1 is to-be-used, the needle point 111 is inserted into the rear end of the needle point cap 30, that is, the needle point 111 is located in the needle point cap 30, which protects the people from injury caused by error launching. Therefore, the blood collection needle 1 provided by embodiments of the present disclosure has good safety performance.

In some embodiments, the needle point cap 30 and the needle core 40 are disposed separately, the rear end of the needle point cap 30 abuts against the front end of the needle core 40, and the protective cap 20 is in an interference fit with the front end of the cylinder body 10. The interference fit between the protective cap 20 and the front end of the cylinder body 10 may prevent the protection cap 20 from disengaging easily from the cylinder body 10, and the operator needs to use a certain force to pull the protection cap 20 from the cylinder body 10, which improves the safety of the blood collection needle 1.

In some other embodiments, at least one of the needle point cap 30 and the needle core 40 has a breakable portion 31, and the front end of the needle core 40 is integrally connected with the rear end of the needle point cap 30 through the breakable portion 31. That is, the needle point cap 30 and the needle core 40 are integrally formed, and the connection between the needle point cap 30 and the needle core 40 is the breakable portion 31. The breakable portion 31 is disconnected when the protective cap 20 drives the needle point cap 30 to move, so that the needle point cap 30 may disengage from the needle point 111. That is to say, the breakable portion 31 is configured to connect the needle point cap 30 and the needle core 40, and may be disconnected when the protective cap 20 drives the needle point cap 30 to move. In an embodiment of the present disclosure, the protective cap 20 may not be in the interference fit with the front end of the cylinder body 10 in case that the needle point cap 30 and the needle core 40 are integrally formed, and the protective cap 20 will not be disengaged easily from the cylinder body 10 under the role of the needle point cap 30. Alternatively, the operator may disconnect the breakable portion 31 more quickly with less force by rotating the protective cap 20, and pull off the protective cap 20.

In some embodiments, in order to realize the linkage between the protective cap 20 and the needle point cap 30, the front end of the needle point cap 30 is provided with a first limiting portion, the inner peripheral wall of the protective cap 20 is provided with a second limiting portion, and the first limiting portion is locked with the second limiting portion, so that the protective cap 20 and the needle point cap 30 are limited to each other to realize the linkage.

Furthermore, the first limiting portion and the second limiting portion are locked to limit a relative translation of the needle point cap 30 and the protective cap 20 in the front-rear direction, and a relative rotation along the protective cap 20 in a circumferential direction. That is to say, since the first limiting portion and the second limiting portion are locked with each other, the needle point cap 30 and the protective cap 20 are limited to each other in the front-back direction, and are limited to each other in the circumferential direction around the protective cap 20, implementing the more reliable linkage relationship between the needle point cap 30 and the protective cap 20. Rotating the protective cap 20 may drive the needle point cap 30 to rotate, and moving the protective cap 20 forward may drive the needle point cap 30 to move forward.

The structures of the protective cap 20 and the needle point cap 30 in an embodiment of the present disclosure will be described below according to reference to FIGS. 1 to 17.

As shown in FIG. 14, the needle point cap 30 of the blood collection needle 1 in an embodiment has the breakable portion 31, and the front end of the needle core 40 is integrally connected with the rear end of the needle point cap 30 through the breakable portion 31. Most part of the needle body 110 is embedded in the needle core 40, and the needle point 111 protruding from the front end of the needle core 40 is located in the needle point cap 30. The breakable portion 31 is disconnected when the protective cap 20 drives the needle point cap 30 to move, that is, the needle point cap 30 and the needle core 40 are separated. The separation of the needle point cap 30 and the needle core 40 may allow the needle point cap 30 to disengage from the needle point 111, making the needle point 111 be exposed. Alternatively, the operator may drive the needle point cap 30 to rotate by rotating the protective cap 20, and the needle point cap 30 rotates relative to the needle core 40 to disconnect the breakable portion 31 more quickly and with less force.

It is understood that, in an embodiment, the protective cap 20 may or may not be in interference fit with the front end of the cylinder body 10. Since the needle point cap 30 and the needle core 40 are integrally formed, under the role of the needle point cap 30, even if the protective cap 20 is not in the interference fit with the front end of the cylinder body 10, the protection cap 20 will not be disengaged easily from the cylinder body 10. Alternatively, an inner diameter of the protective cap 20 is equal to an outer diameter of the front end of the cylinder body 10, so as to prevent the protective cap 20 from shaking relative to the cylinder body 10 and make the protective cap 20 be disengaged from the cylinder body 10 easier, reducing the burden on the operator.

As shown in FIG. 4, the rear end of the needle point cap 30 extends into the cylinder body 10, and the front end of the needle point cap 30 is located outside the cylinder body 10. The front end of the needle point cap 30 is provided with the first limiting portion, and the inner peripheral wall of the protective cap 20 is provided with the second limiting portion that is locked with the first limiting portion. In an embodiment, the first limiting portion is a locking groove 32 disposed on the outer peripheral wall of the needle point cap 30, the second limiting portion is an elastic locking claw 21 disposed on the inner peripheral wall of the protective cap 20. The elastic locking claw 21 extends inward from the inner peripheral wall of the protection cap 20, and a free end of the elastic locking claw 21 is locked in the locking groove 32. In an embodiment, the linkage between the protective cap 20 and the needle point cap 30 is implemented through locking the elastic locking claw 21 and the locking groove 32. In an embodiment, a relative translation of the needle point cap 30 and the protective cap 20 in the front-rear direction and a relative rotation along the protective cap 20 in the circumferential direction are implemented, that is, a rotation of the protective cap 20 may drive a rotation of the needle point cap 30, and a translation of the protective cap 20 in the front-rear direction may drive a translation of the needle point cap 30.

Furthermore, in order to facilitate the assembly of the protective cap 20 and the needle point cap 30, the elastic locking claw 21 extends obliquely forward from the inner peripheral wall of the protective cap 20. When the protective cap 20 is assembled, the protective cap 20 is moved backward relative to the needle point cap 30, and the elastic locking claw 21 is deformed and finally locked into the locking groove 32 on the needle point cap 30, so that the blood collection needle 1 provided by embodiments of the present disclosure may be conveniently assembled and has a reasonable structure.

As shown in FIG. 13, the needle point cap 30 is provided with two locking grooves 32, and the two locking grooves 32 are opposite in a radial direction of the needle point cap 30. The protective cap 20 is provided with two elastic locking claws 21, and the two elastic locking claws 21 are opposite up-down in the radial direction of the protective cap 20. The elastic locking claws 21 are fitted in the locking grooves 32 in a one-to-one correspondence.

It is understood that, in other embodiments, a number of the locking grooves 32 and the elastic locking claws 21 may be more than two. The plurality of the locking grooves 32 are disposed at intervals in the circumferential direction of the needle point cap 30, and the plurality of the elastic locking claws 21 are disposed at intervals in the circumferential direction of the protective cap 20. The elastic locking claws 21 are fitted in the locking grooves 32 in the one-to-one correspondence.

Furthermore, as shown in FIGS. 13 and 14, a step 33 is provided on an outer peripheral wall of the front end of the needle point cap 30, and a locking deck 22 configured to stop the step 33 is provided on the inner peripheral wall of the protective cap 20. In an embodiment, two locking decks 22 are provided and both are fan-shaped, the two locking decks 22 are opposite to each other and spaced apart from each other in the radial direction of the protective cap 20. The front end of the needle point cap 30 is formed as a flat portion 34, and the flat portion 34 is fitted between the two locking decks 22. In an embodiment, two opposite steps 33 are provided on the peripheral wall of the front end of the needle point cap 30, so that the flat portion 34 is formed at the front end of the needle point cap 30, and the flat portion 34 has two opposite side surfaces. The flat portion 34 is fitted between the two locking decks 22, so that the two opposite side surfaces each correspond to the free ends of the two locking decks 22 one-to-one. In this way, a mutual limiting relationship between the protective cap 20 and the needle point cap 30 in the circumferential direction around the protective cap 20 is improved, making the mechanism of the blood collection needle 1 more reasonable.

It is understood that, in order to separate the needle core 40 from the needle point cap 30, the needle core 40 should not rotate with the needle point cap 30. In an embodiment of the present disclosure, the needle core 40 and the cylinder body 10 are limited in the circumferential direction of the cylinder body 10. As shown in FIG. 13, the inner peripheral wall of the cylinder body 10 is provided with a cylinder body chute 130 extending in the front-rear direction, the needle core 40 has a sliding wing 42. The sliding wing 42 is slidably fitted in the cylinder body chute 130. Since the sliding wing 42 is fitted in the cylinder body chute 130, the needle core 40 is limited to rotate.

The following describes an operation process of the blood collection needle 1 of embodiments of the present disclosure according to FIG. 4 to FIG. 8.

As shown in FIG. 4, the blood collection needle 1 is in a non-launched state, the protective cap 20 is fitted over the cylinder body 10, the needle point 111 extends into the rear end of the needle point cap 30, the launch sleeve 60 is located in the first position, the front end of the launch sleeve 60 protrudes from the front end of the cylinder body 10, the rear end of the convex strip 120 engages in the tooth groove 72, and the front end of the limiting portion 41 of the needle core 40 abuts against the stop boss 74 of the connecting ring 70.

Figure 5:
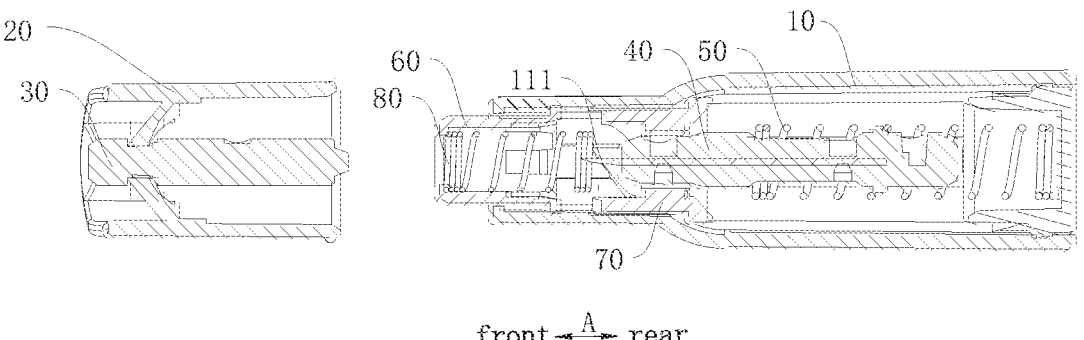
FIG. 5 is a cross-sectional view of a blood collection needle according to an embodiment of the present disclosure.

As shown in FIG. 5, the protective cap 20 is rotated to drive a needle point cap 30 to rotate. The sliding wing 42 is fitted in a cylinder body chute 130. The needle core 40 and the cylinder body 10 are limited to each other in a circumferential direction, and the needle core 40 and the needle body 111 do not rotate. As the needle point cap 30 rotates relative to the needle core 40, the breakable portion 31 is disconnected, and the protective cap 20 moves forward to disengage from the cylinder body 10, meanwhile the needle point cap 30 moves forward relative to the needle core 40. In this process, the needle point 111 located in the needle point cap 30 moves backward relative to the needle point cap 30, disengages gradually from the needle point cap 30, and finally reaches a completely disengaged state shown in FIG. 5. At this time, the needle point 111 is exposed.

Figure 7:
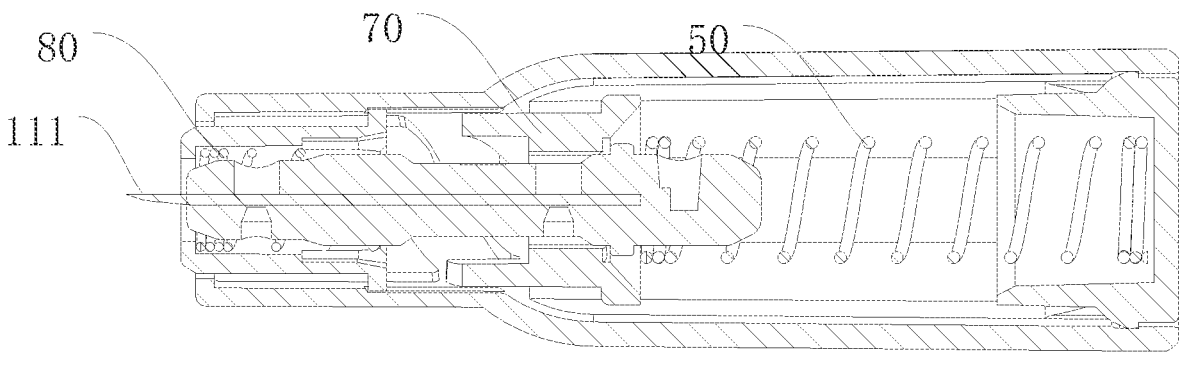
FIG. 7 is a cross-sectional view of a blood collection needle according to an embodiment of the present disclosure.
Figure 8:
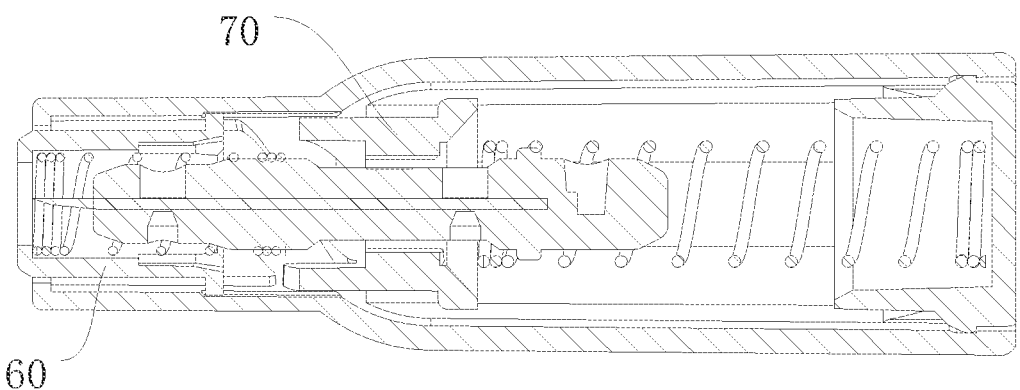
FIG. 8 is a cross-sectional view of a blood collection needle according to an embodiment of the present disclosure.

The front end of the launch sleeve 60 is put against the skin, and the cylinder body 10 is held to push the cylinder body 10 forward, so that the launch sleeve 60 moves backward relative to the cylinder body 10 to reach the second position in FIG. 6 from the first position. In this process, the pushing portion 61 of the launch sleeve 60 drives the teeth 71 of the connecting ring 70 to move backward, so that the connecting ring 70 moves backward. The front end of the limiting portion 41 of the needle core 40 abuts against the stop boss 74 of the connecting ring 70, and the needle core 40 moves backward under the stop of the connecting ring 70 and compresses the launch spring 50. After reaching the second position in FIG. 6, an elastic locking protrusion 64 of the launch sleeve 60 is locked on the step portion 140 of the cylinder body 10, and the step portion 140 limits the launch sleeve 60 from moving forward. The convex strip 120 is disengaged completely from the tooth groove 72. Under the pressure of the launch spring 50, the front end surface of the teeth 71 slides relative to the rear end surface of the pushing portion 61, at the same time the teeth 71 slides forward gradually along an inclined rear end surface of the convex strip 120, and the connecting ring 70 rotates. After the connecting ring 70 rotates to the extreme position, the sliding guide groove 75 on the connecting ring 70 is opposite to the limiting groove 63 on the launch sleeve 60 in the front-rear direction. Since the sliding wing 42 of the needle core 40 is fitted in the cylinder body chute 130 of the cylinder body 10, the needle core 40 will not slide relative to the cylinder body 10, therefore the limiting portion 41 of the needle core 40 is disengaged from the stop boss 74. Under the pressure of the launch spring 50, the needle core 40 is launched forward, and the limiting portion 41 of the needle core 40 slides forward along the sliding guide groove 75 and the limiting groove 63 until it abuts against the bottom of the limiting groove 63 to reach a state in FIG. 7. In FIG. 7, the needle core 40 is launched forward to reach an extreme position, a needle head of the needle body 110 is exposed from the front end of the launch sleeve 60, and the needle head is inserted into the skin as the front end of the launch sleeve 60 abuts against the skin. Moreover, during a forward launching process of the needle core 40, the front end of the limiting portion 41 presses the rear end of the needle withdrawal spring 80 to compress the needle withdrawal spring 80. When the needle core 40 reaches the extreme position shown in FIG. 7, the needle core 40 moves backward under a role of the needle withdrawal spring 80 until reaching a state in FIG. 8. As shown in FIG. 8, the needle core 40 moves backward under a role of the needle withdrawal spring 80 until the needle head retracts into the launch sleeve 60. It is understood that the blood collection needle 1 provided in embodiments of the present disclosure is a disposable blood collection needle.

The blood collection needle 1 includes a rear cover 90, and the rear cover 90 is configured to load from the rear end of the cylinder body 10 to cover an opening on the rear end of the cylinder body 10. An assembling process of the blood collection needle 1 of embodiments of the present disclosure will be described below, for example, FIG. 4.

The launch sleeve 60, the needle withdrawal spring 80, the connecting ring 70, the needle core 40, and the launch spring 50 are loaded into the cylinder body 10 in sequence from the rear end of the cylinder body 10 from back to front, so that the front end of the launch sleeve 60 protrudes from the front end of the cylinder body 10, and the launch spring 50 is located in the first position. The front end of the needle point cap 30 protrudes from the front end of the launch sleeve 60. The rear cover 90 is loaded from the rear end of the cylinder body 10 to cover the opening on the rear end of the cylinder body 10. The protective cap 20 is fitted over the front end of the cylinder body 10 from front to back, so that the elastic locking claw 21 of the protective cap 20 is locked with the locking groove 32 of the needle point cap 30, and the flat portion 34 of the front end of the needle point cap 30 is fitted in the two locking decks 22 of the protective cap 20, so as to complete the assembly.

The blood collection needle provided by the present disclosure skillfully implements a launch of the needle core in the cylinder body through the cylinder body, the launch spring, the launch sleeve and the connecting ring that interact with each other. When the blood collection needle is not in use, the teeth on the cylinder body, the connecting ring and the needle core stop against each other so that the needle body and its needle point are hidden safely inside the cylinder body, and the safety is high. When the blood collection needle is in use, the cylinder body is only needed to hold, making the front end of the launch sleeve touch the skin, and moving the cylinder body forward to make the launch sleeve and the cylinder body slide relative to each other, so that the needle core and the needle body may be launched with the simple operation, the reasonable structure and the reliable performance.

In the specification, it is understood that terms such as "central," "longitudinal," "lateral," "length," "width," "thickness," "upper," "lower," "front," "rear," "left," "right," "vertical," "horizontal," "top," "bottom," "inner," "outer," "clockwise," and "counterclockwise" should be construed to refer to the orientation as then described or as shown in the drawings under discussion. These relative terms are for convenience of description and do not require that the present disclosure be constructed or operated in a particular orientation.

In addition, terms such as "first" and "second" are used herein for purposes of description and are not intended to indicate or imply relative importance or significance or to imply the number of indicated technical features. Thus, the feature defined with "first" and "second" may comprise one or more of this feature. In the description of the present disclosure, "a plurality of" means two or more than two, unless specified otherwise.

In the present disclosure, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art according to specific situations.

In the present disclosure, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed there between. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

Reference throughout this specification to "an embodiment," "some embodiments," "an example," "a specific example," or "some examples," means that a particular feature, structure, material, or characteristic described in connection with the embodiment or example is included in at least one embodiment or example of the present disclosure. Thus, the appearances of the phrases in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can combine the different embodiments or examples and the features described thereof in this specification without mutually inconsistent.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A blood collection needle, comprising:
   a cylinder body provided with a needle core and a needle body therein, wherein the needle body is disposed in the needle core and a needle point of the needle body protrudes from a front end of the needle core, and a convex strip extending in a front-rear direction is disposed on an inner peripheral wall of the cylinder body;
   a launch spring disposed in the cylinder body, stopped against between the cylinder body and the needle core, and configured to press the needle core forward;
   a launch sleeve having a pushing portion, disposed in the cylinder body and movable from a first position to a second position in the front-rear direction; and
   a connecting ring disposed in the cylinder body and located in rear of the launch sleeve;
   wherein a front end of the connecting ring is provided with teeth and a tooth groove between adjacent teeth, and at least one of a rear end surface of the pushing portion and a front end surface of the teeth is an inclined plane;
   wherein in the first position, a front end of the launch sleeve protrudes from a front end of the cylinder body, a rear end of the convex strip engages in the tooth groove, and the connecting ring stops the needle core from moving forward;
   wherein when the launch sleeve moves from the first position to the second position, the pushing portion drives the connecting ring to move backward by pushing the teeth, the convex strip is disengaged from the tooth groove, and the teeth slide relative to the pushing portion under a pressure of the launch spring to drive the connecting ring to rotate, such that the connecting ring releases the needle core, and the needle core is launched forward under a push of the launch spring.

2. The blood collection needle according to claim 1, wherein a front end surface of the convex strip is an inclined plane; in the second position, the teeth slide gradually relative to the pushing portion to engage with the inclined plane of the convex strip, so that at least one of the convex strip and the pushing portion engages in the tooth groove to stop the connecting ring from moving forward when the needle core is launched forward.

3. The blood collection needle according to claim 2, wherein the rear end surface of the pushing portion and a top surface of the teeth are inclined planes.

4. The blood collection needle according to claim 1, wherein
   the launch sleeve comprises a sleeve body, and the pushing portion is disposed on an outer peripheral wall of the sleeve body and extends backward beyond a rear end surface of the sleeve body;
   the pushing portion is a bar-shaped block, the pushing portions are disposed in pairs, and the paired pushing portions are disposed opposite to each other in a radial direction of the sleeve body; and
   a plurality of convex strips are provided and distributed at intervals in a circumferential direction of the cylinder body, and the pushing portion is slidably fitted in a fitting groove between adjacent convex strips.

5. The blood collection needle according to claim 1, wherein a plurality of teeth are provided and distributed at even intervals in a circumferential direction of the connecting ring.

6. The blood collection needle according to claim 1, wherein the needle core is provided with a limiting portion, and a stop boss is disposed on an inner peripheral wall of the connecting ring and stops the limiting portion in the first position, and the limiting portion is disengaged from the stop boss in the second position.

7. The blood collection needle according to claim 6, wherein a rear end surface of the stop boss is an inclined plane, the inner peripheral wall of the connecting ring has a sliding guide groove between the stop bosses, and the limiting portion slides forward along the sliding guide groove when the needle core is launched forward.

8. The blood collection needle according to claim 7, wherein an inner peripheral wall of the launch sleeve is provided with a limiting groove for limiting an extreme position of a forward movement of the needle core, and the limiting portion enters the limiting groove and slides forward along the limiting groove to the extreme position when the needle core is launched forward.

9. The blood collection needle according to claim 1, wherein the inner peripheral wall of the cylinder body is provided with a cylinder body chute extending in the front-rear direction, the needle core has a sliding wing, and the sliding wing is slidably fitted in the cylinder body chute.

10. The blood collection needle according to claim 1, wherein a step portion is provided on the inner peripheral wall of the cylinder body, and the launch sleeve has an elastic locking protrusion; when the launch sleeve moves from the first position to the second position, the elastic locking protrusion is locked by the step portion to prevent the launch sleeve from moving forward during forward launching of the needle core.

11. The blood collection needle according to claim 1, comprising a needle withdrawal spring;

wherein the needle withdrawal spring is disposed in the launch sleeve, and a front end of the needle withdrawal spring stops against the launch sleeve; the needle core gradually compresses the needle withdrawal spring when the needle core is launched forward, and the needle withdrawal spring pushes the needle core to move backward after the needle core moves forward to an extreme position, so that the needle point of the needle body is retracted into the launch sleeve and/or the cylinder body.

12. The blood collection needle according to claim 1, comprising a protective cap and a needle point cap;

wherein the protective cap is detachably fitted over the front end of the cylinder body, a rear end of the needle point cap extends into the cylinder body from the front end of the cylinder body, the needle point is inserted into the rear end of the needle point cap, and the needle point cap is disposed in the protective cap and linked with the protective cap, so that the protective cap drives the needle point cap to disengage from the needle point when the protective cap is disengaged from the cylinder body.

13. The blood collection needle according to claim 12, wherein at least one of the needle point cap and the needle core has a breakable portion, the front end of the needle core and the rear end of the needle point cap are integrally connected through the breakable portion, and the breakable portion is broken to allow the needle point cap to disengage from the needle point when the protective cap drives the needle point cap to move.

14. The blood collection needle according to claim 12, wherein the needle point cap is disposed separately from the needle core, the rear end of the needle point cap abuts against the front end of the needle core, and the protective cap is in an interference fit with the cylinder body.

15. The blood collection needle according to claim 12, wherein a front end of the needle point cap is provided with a first limiting portion, an inner peripheral wall of the protective cap is provided with a second limiting portion, and the first limiting portion is locked with the second limiting portion so that the needle point cap is linked with the protective cap.

16. The blood collection needle according to claim 15, wherein the first limiting portion and the second limiting portion are locked to limit a relative translation of the needle point cap and the protective cap in the front-rear direction and a relative rotation of the needle point cap and the protective cap in a circumferential direction of the protective cap.

17. The blood collection needle according to claim 16, wherein the first limiting portion is a locking groove formed in an outer peripheral wall of the needle point cap, the second limiting portion is an elastic locking claw disposed on the inner peripheral wall of the protective cap, and a free end of the elastic locking claw is locked in the locking groove.

18. The blood collection needle according to claim 17, wherein the elastic locking claw extends obliquely forward from the inner peripheral wall of the protective cap.

19. The blood collection needle according to claim 17, wherein a plurality of locking grooves are provided and disposed at intervals around a circumferential direction of the needle point cap, a plurality of elastic locking claws are provided and disposed at intervals around the circumferential direction of the protective cap, and the elastic locking claws are fitted in the locking grooves in a one-to-one correspondence.

20. The blood collection needle according to claim 16, wherein a step is provided on an outer peripheral wall of the front end of the needle point cap, and a locking deck for stopping the step is provided on the inner peripheral wall of the protective cap;

the locking deck is fan-shaped, two locking decks are provided opposite to each other and spaced apart from each other, the front end of the needle point cap is formed as a flat portion, and the flat portion is fitted between the two locking decks.

* * * * *